(12) United States Patent
Penman, Jr.

(10) Patent No.: US 8,977,115 B2
(45) Date of Patent: Mar. 10, 2015

(54) VAPORIZER WITH SECONDARY FLOW PATH

(71) Applicant: STERIS Inc., Temecula, CA (US)

(72) Inventor: Leslie Woodson Penman, Jr., Garfield Heights, OH (US)

(73) Assignee: STERIS Inc., Temecula, CA (US)

( * ) Notice: Subject to any disclaimer, the term of this patent is extended or adjusted under 35 U.S.C. 154(b) by 123 days.

(21) Appl. No.: 13/790,567

(22) Filed: Mar. 8, 2013

(65) Prior Publication Data
US 2014/0255012 A1 Sep. 11, 2014

(51) Int. Cl.
F22B 1/20 (2006.01)
F22B 29/06 (2006.01)
F24F 3/14 (2006.01)
A61L 9/03 (2006.01)

(52) U.S. Cl.
CPC ........................................ A61L 9/03 (2013.01)
USPC ........... 392/386; 392/391; 392/394; 392/396; 392/398

(58) Field of Classification Search
None
See application file for complete search history.

(56) References Cited

U.S. PATENT DOCUMENTS

| | | | | |
|---|---|---|---|---|
| 2,303,948 A * | 12/1942 | Morris | | 126/113 |
| 3,689,037 A * | 9/1972 | Payne | | 261/105 |
| 3,990,427 A * | 11/1976 | Clinebell | | 126/113 |
| 4,056,582 A * | 11/1977 | Chow | | 261/30 |
| 4,178,334 A * | 12/1979 | Miller | | 261/142 |
| 4,375,799 A * | 3/1983 | Swanson | | 123/549 |
| 4,742,667 A | 5/1988 | Müller et al. | | 53/167 |
| RE33,414 E * | 10/1990 | Morton | | 392/386 |
| 5,075,047 A * | 12/1991 | Youngeberg | | 261/100 |
| 5,096,615 A * | 3/1992 | Prescott et al. | | 516/1 |
| 5,109,916 A * | 5/1992 | Thompson | | 165/59 |
| 5,224,202 A | 6/1993 | Arnold et al. | | 392/399 |
| 5,693,267 A * | 12/1997 | Beshore et al. | | 261/142 |
| 5,702,648 A * | 12/1997 | White et al. | | 261/142 |
| 5,758,018 A * | 5/1998 | Fowler, Jr. | | 392/402 |
| 5,835,677 A | 11/1998 | Li et al. | | 392/401 |
| 5,876,664 A | 3/1999 | Childers et al. | | 422/28 |
| 6,746,652 B2 | 6/2004 | Khorzad et al. | | 422/305 |
| 7,320,459 B2 * | 1/2008 | Johns | | 261/142 |
| 7,713,473 B2 * | 5/2010 | Kendall et al. | | 422/28 |
| 8,071,021 B2 | 12/2011 | Hill | | 422/28 |
| 8,128,069 B2 * | 3/2012 | Reens | | 261/30 |
| 2004/0182855 A1 * | 9/2004 | Centanni | | 219/628 |
| 2006/0086814 A1 * | 4/2006 | Helt et al. | | 236/44 A |
| 2007/0098592 A1 | 5/2007 | Buczynski et al. | | 422/3 |
| 2011/0155131 A1 | 6/2011 | Bottom | | 128/203.14 |
| 2012/0180724 A1 * | 7/2012 | Kouketsu et al. | | 118/712 |

* cited by examiner

*Primary Examiner* — Thor Campbell
(74) *Attorney, Agent, or Firm* — Kusner & Jaffe; Michael A. Centanni

(57) ABSTRACT

A vaporizer for generating a vaporized chemical decontaminating agent. The vaporizer includes a primary flow path and a blower for conveying a carrier gas along the primary flow path. A secondary flow path has a first end fluidly connected to the primary flow path at a location upstream of the blower and a second end fluidly connected to the primary flow path at a location downstream of the blower. A heating element is disposed along the secondary flow path. A liquid flow path has a first end fluidly connected to a source of liquid chemical decontaminating agent and a second end fluidly connected to the secondary flow path. The liquid flow path injects the liquid chemical decontaminating agent into the secondary flow path at a location upstream of the heating element. The heating element vaporizes the liquid chemical decontaminating agent to form the vaporized chemical decontaminating agent.

16 Claims, 2 Drawing Sheets

VAPORIZER WITH SECONDARY FLOW PATH

FIELD OF THE INVENTION

The present invention relates to an apparatus for decontaminating a region and articles disposed therein, and more particularly, to a vaporizer for decontaminating a region and articles disposed therein using a vaporous chemical decontaminating agent.

BACKGROUND OF THE INVENTION

A region, defined by an enclosure, (e.g., hotel rooms, offices, laboratories, buildings, cruise ships, airport terminals, and the like) may be decontaminated by exposing the region (and any articles therein) to a vaporous chemical decontaminating agent, such as vaporized hydrogen peroxide. Vaporized hydrogen peroxide may be generated by vaporizing a metered quantity of an aqueous solution of hydrogen peroxide (e.g., about 30% to 59% hydrogen peroxide, by weight). The vaporized hydrogen peroxide is carried into the region by a carrier gas (e.g., air). As used herein the term "decontamination" refers to the inactivation of bio-contamination, and includes, but is not limited to, sterilization and disinfection.

Some systems for vaporizing an aqueous solution of hydrogen peroxide include a heated section wherein all the air flowing through the heated section is heated to a predetermined temperature. These systems tend to waste large amounts of heat during the heating process. Furthermore, the rate of air flowing through such systems tends to be limited because large flow rates of air may cool the system thereby making the system ineffective at vaporizing an aqueous solution of hydrogen peroxide.

To address the foregoing issues, some systems inject the aqueous solution of hydrogen peroxide into a stream of heated air. The heated air causes the aqueous solution of hydrogen peroxide to vaporize upon injection therein. However, the foregoing evaporation process tends to require relatively large heaters to heat the air. These systems thus tend to require relatively large amounts of power (e.g., 10,000 watts) to generate the vaporized hydrogen peroxide. In addition, when the aqueous solution of hydrogen peroxide is injected into the air it is often difficult to prevent the droplets of hydrogen peroxide from contacting the walls of the system and coalescing into a film. Due to the corrosive characteristics of hydrogen peroxide, films of liquid hydrogen peroxide in the system may create a dangerous condition.

The present invention overcomes the aforementioned problem and provides an apparatus that effectively and efficiently vaporizes hydrogen peroxide at an ambient air temperature of a region.

SUMMARY OF THE INVENTION

In accordance with a preferred embodiment of the present invention, there is provided a vaporizer for generating a vaporized chemical decontaminating agent. The vaporizer includes a primary flow path and a blower for conveying a carrier gas along the primary flow path. A secondary flow path has a first end fluidly connected to the primary flow path at a location upstream of the blower and a second end fluidly connected to the primary flow path at a location downstream of the blower. A heating element is disposed along the secondary flow path. A liquid flow path has a first end fluidly connected to a source of liquid chemical decontaminating agent and a second end fluidly connected to the secondary flow path. The liquid flow path injects the liquid chemical decontaminating agent into the secondary flow path at a location upstream of the heating element. The heating element vaporizes the liquid chemical decontaminating agent to form the vaporized chemical decontaminating agent.

In accordance with another preferred embodiment of the present invention, there is provided a method for generating a vaporized chemical decontaminating agent. The method includes steps of:
  conveying a carrier gas along a primary flow path;
  conveying a portion of the carrier gas along a secondary flow path wherein a first end of the secondary flow path is fluidly connected to the primary flow path at a first location and a second end of the secondary flow path is fluidly connected to the primary flow path at a second location, the second location being upstream of the first location and wherein the carrier gas flows along the secondary flow path from the first end of the secondary flow path to the second end of the secondary flow path;
  injecting a liquid chemical decontaminating agent into the secondary flow path;
  heating the liquid chemical decontaminating agent at a predetermined location along the secondary flow path to form the vaporous chemical decontaminating agent; and
  injecting the vaporous chemical decontaminating agent into the primary flow path at the second location along the primary flow path.

An advantage of the present invention is the provision of an apparatus for decontaminating a region defined by an enclosure using a vaporous chemical decontaminating agent.

Yet another advantage of the present invention is the provision of an apparatus as described above that requires less power as compared to conventional apparatuses.

Still another advantage of the present invention is the provision of an apparatus as described above that vaporizes the chemical decontaminating agent at the temperature of the ambient air in the region.

Another advantage of the present invention is the provision of an apparatus as described above that does not require heating the ambient air passing through the apparatus.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
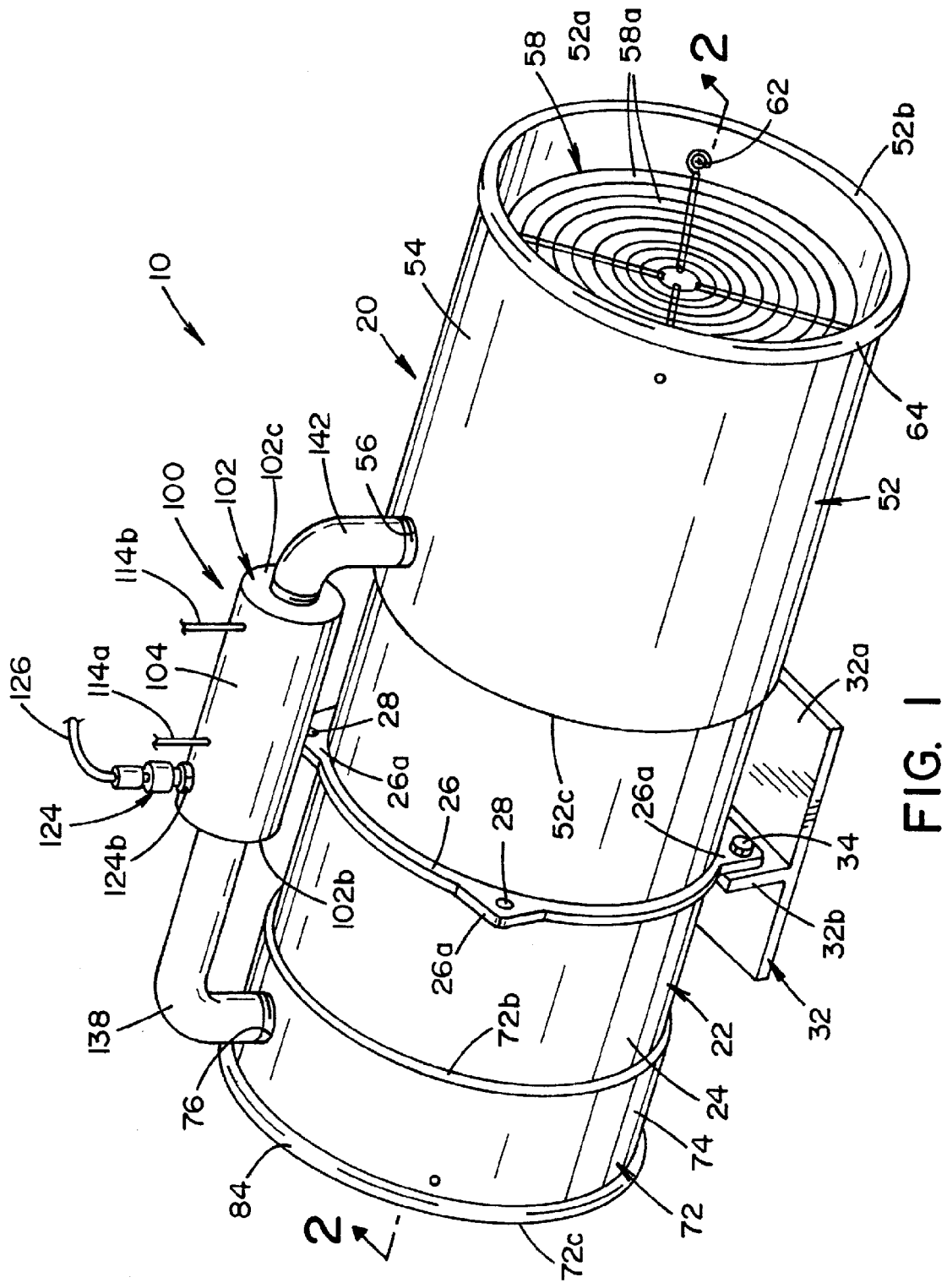
FIG. 1 is a side perspective view of an apparatus for decontaminating a region defined by an enclosure.
Figure 2:
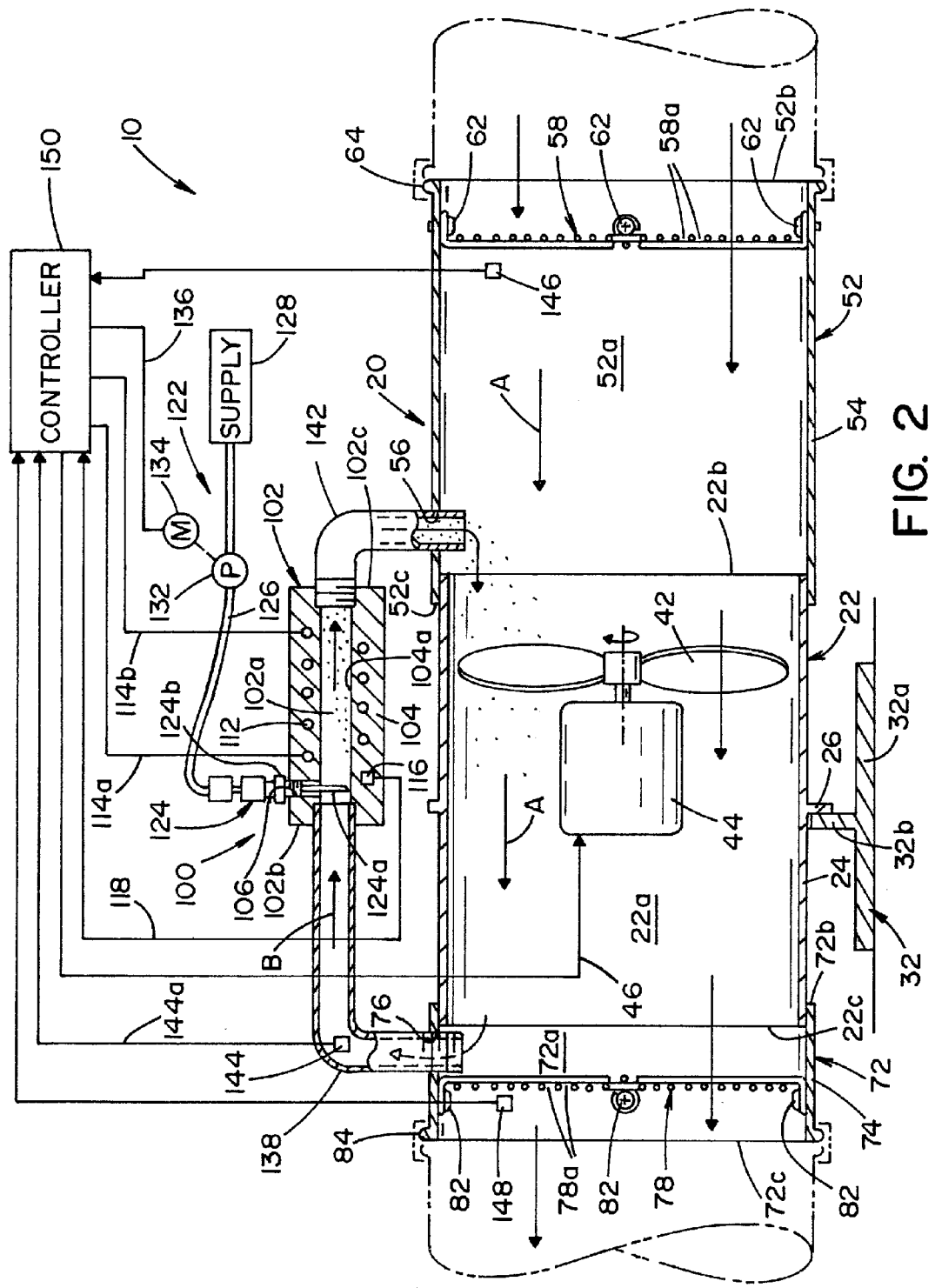
FIG. 2 is a cross-sectional view of the apparatus taken along lines 2-2 in FIG. 1.

Referring now to the drawings wherein the showings are for the purpose of illustrating an embodiment of the invention only, and not for the purpose of limiting same, FIGS. 1 and 2 show a side perspective view and a cross-section view, respectively, of vaporizer 10 for decontaminating a region defined by an enclosure. The present invention will be described hereinafter with reference to generating vaporized hydrogen peroxide to decontaminate a region. However, it is appreciated that vaporizer 10 may be adapted to decontaminate a region with other types of chemical decontaminating agents. Accordingly, it is contemplated that other chemical decontaminating agents may be substituted for hydrogen peroxide in the following description of the present invention.

Vaporizer 10 includes a main flow assembly 20, a vaporization assembly 100 and a controller 150 (shown in FIG. 2).

As shown in FIG. 2, main flow assembly 20 includes a central housing 22, a fan 42, an inlet housing 52 and an outlet housing 72. Central housing 22 is generally tubular in shape and has an outer wall 24. Outer wall 24 defines an opening 22a that extends between an inlet end 22b and an outlet end 22c of central housing 22. In the embodiment shown, outer wall 24 is cylindrical in shape. A flange 26 extends outwardly from an outer surface of outer wall 24 near a central portion of outer wall 24 of central housing 22. Holes 28 (shown in FIG. 2) extend through flange 26. In the embodiment shown, flange 26 includes a plurality of spaced-apart tab portions 26a and holes 28 extend through tab portions 26a of flange 26.

A support bracket 32 is attached to flange 26 of central housing 22 for supporting main flow assembly 20. Bracket 32 includes a flat rectangular portion 32a and a rib portion 32b that extends from a surface of portion 32a, Holes (not shown) extend through rib portion 32b and are dimensioned to align with and be in registry with two (2) holes 28 in flange 26 of central housing 22. Bolts 34 (shown in FIG. 2) extend through holes 28 in flange 26 of central housing 22 and the holes in bracket 32 for securing bracket 32 to central housing 22.

Fan 42 is disposed within opening 22a of central housing 22. A bracket (not shown) attaches fan 42 to central housing 22. Fan 42 is designed for conveying air through opening 22a of central housing 22 at a rate of between about 500 cubic feet per minute (CFM) and 1000 CFM. Fan 42 is driven by a motor 44. A cable 46 connects motor 44 to controller 150 to allow controller 150 to control the operation of motor 44.

Inlet housing 52 is attached to inlet end 22b of central housing 22 of main flow assembly 20. Inlet housing 52 is generally tubular in shape and has an outer wall 54. Outer wall 54 defines an opening 52a that extends between an inlet end 52b and an outlet end 52c of inlet housing 52. In the embodiment shown, outer wall 54 is cylindrical in shape. A threaded hole 56 extends through outer wall 54 of inlet housing 52 near outlet end 52c, A flange 64 extends radially outward from an outer peripheral edge of inlet end 52b, Flange 64 is dimensioned as shall be described in detail below.

A fan guard 58 transverses opening 52a of inlet housing 52 near inlet end 52b of inlet housing 52. Fan guard 58 includes a plurality of openings 58a for allowing air to pass therethrough while hindering debris from passing therethrough. In the embodiment shown, fan guard 58 includes a plurality of wire-shaped elements that are welded together to define openings 58a, Screws 62 secure fan guard 58 to outer wall 54 of inlet housing 52.

Outlet housing 72 is attached to outlet end 22c of central housing 22 of main flow assembly 20. Outlet housing 72 is generally tubular in shape and has an outer wall 74. Outer wall 74 defines an opening 72a that extends between an inlet end 72b and an outlet end 72c of outlet housing 72. In the embodiment shown, outer wall 74 is cylindrical in shape. A threaded hole 76 extends through outer wall 74 of outlet housing 72 near inlet end 72b, A flange 84 extends radially outward from an outer peripheral edge of outlet end 72b, Flange 84 is dimensioned as shall be described in detail below.

A fan guard 78 transverses opening 72a of outlet housing 72 near outlet end 72c, Fan guard 78 includes a plurality of openings 78a for allowing air to pass therethrough while hindering debris from passing therethrough. In the embodiment shown, fan guard 78 includes a plurality of wire-shaped elements that are welded together to define openings 78a, Screws 82 secure fan guard 78 to outer wall 74 of outlet housing 72.

Inlet housing 52 and outlet housing 72 attach to opposite ends of central housing 22. In this respect, inlet housing 52 defines an inlet region of vaporizer 10 and outlet housing 72 defines an outlet region of vaporizer 10. In the embodiment shown, outer wall 54 of inlet housing 52 and outer wall 74 of outlet housing 72 are dimensioned to receive outer wall 24 of central housing 22. Inlet housing 52 and outlet housing 72 are attached to central housing 22 such that opening 52a of inlet housing 52, opening 72a of outlet housing 72 and opening 22a of central housing 22 are in fluid communication with each other to define a primary flow path "A" of vaporizer 10.

In the embodiment shown, main flow assembly 20 includes three (3) separate housings, i.e., inlet housing 52, outlet housing 72 and central housing 22 that together define primary flow path "A" of vaporizer 10. It is contemplated that main flow assembly 20 of vaporizer 10 may include a single housing that defines primary flow path "A" wherein a portion of the single housing defines the inlet region of vaporizer 10 and another portion of the single housing defines the outlet region of vaporizer 10.

Vaporization assembly 100, best seen in FIG. 2, is fluidly connected to main flow assembly 20 of vaporizer 10. Vaporization assembly 100 includes a housing 102 and an injection assembly 122. Housing 102 is generally tubular in shape and has an outer wall 104. An inner surface 104a of outer wall 104 defines a vaporization chamber 102a of vaporization assembly 100. Vaporization chamber 102a extends between an inlet end 102b and an outlet end 102c of housing 102. A threaded hole 106 extends through outer wall 104 of housing 102 near inlet end 102b of housing 102.

A heating element 112 is provided for heating outer wall 104 of housing 102. Heating element 112 preferably heats inner surface 104a of outer wall 104 to a temperature between about 110° C. and about 130° C. In the embodiment shown, heating element 112 is a coil-shaped element that is embedded within outer wall 104 of housing 102. Cables 114a, 114b connect heating element 112 to controller 150 to allow controller 150 to control the operation of heating element 112.

A temperature sensor 116 is disposed proximate to inner surface 104a of outer wall 104. Temperature sensor 116 provides a signal indicative of the temperature of inner surface 104a of outer wall 104. A cable 118 connects temperature sensor 116 to controller 150.

Injection assembly 122 is connected to housing 102 to provide liquid hydrogen peroxide to vaporization chamber 102a of housing 102. Injection assembly 122 includes an injection needle 124, a supply 128 and a pump 132. Injection needle 124 threads into hole 106 of housing 102. Injection needle 124 includes an elongated tube portion 124a and a connecter 124b, Connecter 124b includes threads for threading into hole 106 of housing 102. Connector 124b fluidly connects injection needle 124 to an end of a supply conduit 126. Another end of supply conduit 126 is attached to supply 128. Supply 128 holds a predetermined volume of liquid hydrogen peroxide. Injection assembly 122 is attached to housing 102 such that the distal end of tube portion 124a of injection needle 124 is disposed proximate inner surface 104a of outer wall 104 of housing 102. In the embodiment shown, the distal end of tube portion 124a is in contact with inner surface 104a of housing 102.

Pump 132 is disposed within supply conduit 126 for drawing liquid hydrogen peroxide from supply 128 and pumping liquid hydrogen peroxide to injection needle 124. Pump 132 is driven by a motor 134. A cable 136 connects motor 134 to controller 150 to allow controller 150 to control the operation of motor 134.

A first conduit 138 is connected at one end to hole 76 in outer wall 74 of outlet housing 72 and at another end to inlet end 102b of housing 102 of vaporization assembly 100. First conduit 138 fluidly connects opening 72a of outlet housing 72 to vaporization chamber 102b of housing 102. A second conduit 142 is connected at one end to hole 56 in outer wall 54 of inlet housing 52 and at another end to outlet end 102b of housing 102. Second conduit 142 fluidly connects opening 52a of inlet housing 52 to vaporization chamber 102b of housing 102. First conduit 138, second conduit 142 and vaporization chamber 102b of housing 102 define a secondary fluid path "B" of vaporizer 10. In this respect, an inlet of conduit 138 defines an inlet or first end of secondary flow path "B" and an outlet of second conduit 142 defines an outlet or second end of secondary flow path "B." In addition, hole 76 in outer wall 74 of outlet housing 72 defines a first location along primary flow path "A" where the inlet or first end of secondary flow path "B" connects to primary flow path "A." Similarly, hole 56 in outer wall 54 of inlet housing 52 defines a second location along primary flow path "A" where the outlet or second end of secondary flow path "B" connects to primary flow path "A."

A pressure sensor 144 is disposed within first conduit 138. Pressure sensor 144 provides a signal indicative of the pressure of the air in first conduit 138. A cable 144a connects pressure sensor 144 to controller 150.

Sensor(s) 146 are disposed within inlet housing 52. Similarly, sensor(s) 148 are disposed within outlet housing 72. Sensors 146, 148 may each include a temperature sensor, a humidity sensor and a vaporized hydrogen peroxide (VHP) sensor. The temperature sensor provides a signal indicative of the temperature of the air in inlet housing 52 or outlet housing 72. Humidity sensor provides a signal indicative of the water vapor concentration (e.g., relative humidity (RH)) within inlet housing 52 or outlet housing 72. Absolute humidity may be determined from the temperature and RH sensed respectively by the temperature sensor and the humidity sensor, or alternatively the humidity sensor can take the form of a sensor that directly measures absolute humidity. The VHP sensor provides a signal indicative of the concentration of vaporized hydrogen peroxide in inlet housing 52 or outlet housing 72. The VHP sensor is preferably a near infrared (IR) sensor or an electrochemical sensor.

Controller 150 may include a microprocessor or microcontroller, memory device(s) and a wireless communications interface. An input/output means (not shown) (e.g., a touch screen) is connected to controller 150 for allowing an operator to input commands into controller 150 and to receive output from controller 150. As described above, controller 150 is connected to motors 44, 134, heating element 112, temperature sensor 116 and sensors 144, 146, 148. Controller 150 is programmed to control the operation of unit 10 using motors 44, 134 and heating element 112.

In the embodiment shown, vaporizer 10 is placed outside of a region and conduits (shown in phantom in FIG. 2.) are connected to inlet housing 52 and outlet housing 72 for fluidly connecting vaporizer 10 to the region. In particular, flanges 64, 84 of inlet housing 52 and outlet housing 72, respectively, are dimensioned such that inlet housing 52 and outlet housing 72 may be clamped or secured to the conduits. It is also contemplated that vaporizer 10 may be placed within the region to be decontaminated such that the conduits are not required.

The operation of unit 10 will now be described in connection with the decontamination of articles in the region. Controller 150 is programmed to control the operation of motors 44, 134 and heating element 112 during a decontamination process. Controller 150 initiates the decontamination process by energizing motor 44. Motor 44 turns fan 42 thereby drawing ambient air from the region into vaporizer 10. The ambient air is circulated through main flow assembly 20 along primary flow path "A" and back into the region.

As the ambient air is conveyed along primary flow path "A," fan 42 causes the pressure in the outlet region of vaporizer 10 to be higher than the pressure in the inlet region of vaporizer 10. The difference in the pressure between the inlet region and the outlet region is preferably between about 5 and about 10 inches of water. The difference in the pressure between the inlet region and the outlet region causes ambient air to be drawn through hole 76 of outlet housing 72 into first conduit 138. The ambient air then is forced through vaporization chamber 102a, through second conduit 142 and into inlet housing 52 through hole 56 of inlet housing 52. As such, the ambient air is conveyed along secondary flow path "B." The air exiting secondary flow path "B" then mixes with the air drawn into vaporizer 10 through the inlet region of vaporizer 10. Most of the mixed air is then exhausted through the outlet region of vaporizer 10 and into the region. A portion of the mixed air is drawn back through hole 76 of outlet housing 72 and is conveyed again along secondary flow path "B."

As noted above, fan 42 is designed to convey ambient air along primary flow path "A" at a rate of between about 500 cubic feet per minute (CFM) and about 1000 CFM. It is believed that the foregoing flow rate along primary flow path "A" generates a flow rate of between about 1 and about 10 CFM along secondary flow path "B."

Controller 150 monitors pressure sensor 144 in first conduit 138 as air is conveyed along secondary flow path "B." The pressure in first conduit 138 provides an indication of the rate that air is flowing along secondary flow path "B." When the pressure in first conduit 138 has reached a predetermined pressure, as determined by pressure sensor 144, controller 150 energizes heating element 112 to heat inner surface 104a of housing 102 to a predetermined temperature. As noted above, heating element 112 preferably heats inner surface 104a of housing 102 to a temperature between about 110° C. and about 130° C. When inner surface 104a reaches a predetermined temperature, as measured by temperature sensor 116, controller 150 energizes motor 134 to cause pump 132 to supply the aqueous solution of liquid hydrogen peroxide to injection needle 124 of injection assembly 122. In particular, controller 150 controls the speed of motor 134 to cause pump 132 to supply the aqueous solution of liquid hydrogen peroxide to injection needle 124 at a predetermined flow rate.

The aqueous solution of liquid hydrogen peroxide exits the distal end of injection needle 124 and comes into contact with inner surface 104a of housing 102. In the embodiment shown, housing 102 is oriented such that a central axis of housing 102 is horizontal. According to the illustrated embodiment, the distal end of injection needle 124 is in contact with inner surface 104a of housing 102 such that housing 102 is not limited to the horizontal orientation. It is contemplated that housing 102 may have other orientations without departing from the spirit and scope of the present invention.

Upon contact with inner surface 104a, the liquid hydrogen peroxide vaporizes and forms vaporized hydrogen peroxide (VHP). The VHP is mixed with the air conveyed along secondary flow path "B." In this respect, the ambient air acts as a carrier gas and mixes with the VHP to form an air/VHP mixture. The air/VHP mixture is then exhausted into primary flow path "A" through hole 56 of inlet housing 52. The air/VHP mixture then mixes with the air moving along primary flow path "A." A portion of this mixture is exhausted out of vaporizer 10 through outlet housing 72 and into the region. Another portion of this mixture is drawn back through hole 76 of outlet housing 72 and is conveyed again along secondary flow path "B."

During operation of vaporizer 10, controller 150 continuously monitors sensors 146,148 to determine preselected properties of the air drawn into vaporizer 10 and preselected properties of the air exhausted out of vaporizer 10. Controller 150 is programmed to control motors 44, 134 and heating element 112 to obtain and/or maintain a desired concentration of VHP in the region. In particular, sensor(s) 146, 148 provide feedback to controller 150 thereby allowing controller 150 to control motors 44, 134 and heating element 112 to achieve a desired concentration of VHP in the region. Controller 150 is programmed to control the concentration of VHP in the region by controlling the rate that air flows along primary flow path "A" and secondary flow path "B," the temperature of inner surface 104a of housing 102 and the rate that liquid hydrogen peroxide is conveyed to vaporization chamber 102a of vaporization assembly 100.

The present invention, thus, is designed to vaporize hydrogen peroxide at the ambient air temperature in the region. As a result, the present invention requires less power to decontaminate a region as compared to conventional systems. Conventional systems for vaporizing hydrogen peroxide require large amounts of power to heat a carrier gas, thereby limiting their use to applications where large amounts of electrical energy are available.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A vaporizer for generating a vaporized chemical decontaminating agent to decontaminate a region, said vaporizer comprising:
   a primary flow path having an inlet end and an outlet end;
   a blower for conveying a carrier gas along said primary flow path;
   a secondary flow path having a first end fluidly connected to said primary flow path at a location between said outlet end of said primary flow path and said blower and a second end fluidly connected to said primary flow path at a location between said inlet end of said primary flow path and said blower, wherein said carrier gas flows from said first end of said secondary flow path to said second end of said secondary flow path;
   a heating element disposed along said secondary flow path; and
   a liquid flow path having a first end fluidly connected to a source of liquid chemical decontaminating agent and a second end fluidly connected to said heating element, wherein said heating element vaporizes said liquid chemical decontaminating agent to form said vaporized chemical decontaminating agent.

2. The vaporizer for generating a vaporized sterilant, as defined in claim 1, said vaporizer further comprising:
   at least one upstream sensor disposed along said primary flow path at a location upstream of said blower; and
   at least one downstream sensor disposed along said primary flow path at a location downstream of said blower.

3. The vaporizer for generating a vaporized chemical decontaminating agent, as defined in claim 2, wherein said at least one upstream sensor includes at least one of a chemical decontaminating agent concentration sensor, a temperature sensor or a humidity sensor.

4. The vaporizer for generating a vaporized chemical decontaminating agent, as defined in claim 2, wherein said at least one downstream sensor includes at least one of a chemical decontaminating agent concentration sensor, a temperature sensor or a humidity sensor.

5. The vaporizer for generating a vaporized chemical decontaminating agent, as defined in claim 1, wherein said inlet end and said outlet end of said primary flow path fluidly communicates with a region to define a closed-loop system.

6. The vaporizer for generating a vaporized chemical decontaminating agent, as defined in claim 1, wherein the flow rate of the carrier gas through said primary flow path is between about 500 and about 1000 cubic feet per minute and the flow rate of the carrier gas along said secondary flow path is between about 1 and about 10 cubic feet per minute.

7. The vaporizer for generating a vaporized chemical decontaminating agent, as defined in claim 1, wherein said liquid chemical decontaminating agent is an aqueous solution of hydrogen peroxide.

8. The vaporizer for generating a vaporized chemical decontaminating agent, as defined in claim 1, wherein said primary flow path is free of a heating element.

9. A method for generating a vaporous chemical decontaminating agent to decontaminate a region, said method including steps of:
   conveying a carrier gas along a primary flow path, said primary flow path having an inlet end and an outlet end;
   conveying a portion of said carrier gas along a secondary flow path, wherein a first end of said secondary flow path is fluidly connected to said primary flow path at a first location and a second end of said secondary flow path is fluidly connected to said primary flow path at a second location, said second location being upstream of said first location and wherein said carrier gas flows along said secondary flow path from said first end of said secondary flow path to said second end of said secondary flow path;
   injecting a liquid chemical decontaminating agent into a heating element disposed along said secondary flow path;
   heating said liquid chemical decontaminating agent to form said vaporous chemical decontaminating agent; and
   injecting said vaporous chemical decontaminating agent into said primary flow path at said second location along said primary flow path.

10. The method for generating a vaporous chemical decontaminating agent, as defined in claim 9, wherein a fan is disposed along said primary flow path between said first location and said second location.

11. The method for generating a vaporous chemical decontaminating agent, as defined in claim 9, further including a step of:

measuring a first property of said carrier gas at a location upstream of said second location and measuring a second property of said carrier gas at a location downstream of said first location.

12. The method for generating a vaporous chemical decontaminating agent, as defined in claim 11, wherein said first property of said carrier gas includes at least one of the following: a temperature, a humidity or a concentration of said vaporous chemical decontaminating agent.

13. The method for generating a vaporous chemical decontaminating agent, as defined in claim 12, wherein said second property of said carrier gas includes at least one of the following: a temperature, a humidity or a concentration of said vaporous chemical decontaminating agent.

14. The method for generating a vaporous chemical decontaminating agent, as defined in claim 11, further comprising a step of:
    adjusting at least one of said steps of
        conveying a carrier gas along a primary flow path,
        injecting a liquid chemical decontaminating agent into a heating element, and
        heating said liquid chemical decontaminating agent,
    based on said first property of said carrier gas and said second property of said carrier gas.

15. The method for generating a vaporous chemical decontaminating agent, as defined in claim 9, wherein said liquid chemical decontaminating agent is an aqueous solution of hydrogen peroxide.

16. The method for generating a vaporous chemical decontaminating agent, as defined in claim 9, wherein said primary flow path is free of a heating element.

* * * * *